(12) United States Patent
Nicolas et al.

(10) Patent No.: US 9,234,903 B2
(45) Date of Patent: *Jan. 12, 2016

(54) HEPCIDIN INHIBITORS FOR REGULATING IRON HOMEOSTASIS

(75) Inventors: Gaël Nicolas, Paris (FR); Sophie Vaulont, Paris (FR); Axel Kahn, Paris (FR)

(73) Assignee: INSERM (INSTITUT NATIONAL DE LA SANTÉ ET DE LA RECHERCHE MÉDICALE, Paris (FR)

( * ) Notice: Subject to any disclaimer, the term of this patent is extended or adjusted under 35 U.S.C. 154(b) by 1090 days.

This patent is subject to a terminal disclaimer.

(21) Appl. No.: 11/602,402

(22) Filed: Nov. 21, 2006

(65) Prior Publication Data

US 2007/0124825 A1 May 31, 2007

Related U.S. Application Data

(62) Division of application No. 10/478,987, filed as application No. PCT/EP02/06924 on May 24, 2002, now Pat. No. 7,169,758.

(30) Foreign Application Priority Data

| May 25, 2001 | (EP) | ..................... 01401377 |
| Jun. 14, 2001 | (EP) | ..................... 01401537 |
| Mar. 29, 2002 | (EP) | ..................... 02290795 |

(51) Int. Cl.
*G01N 33/90* (2006.01)
*A61K 38/17* (2006.01)

(52) U.S. Cl.
CPC ............ *G01N 33/90* (2013.01); *A61K 38/1709* (2013.01)

(58) Field of Classification Search
None
See application file for complete search history.

(56) References Cited

U.S. PATENT DOCUMENTS

| 6,465,719 | B1 * | 10/2002 | DeRose et al. ................. 800/301 |
| 7,169,758 | B2 * | 1/2007 | Nicolas et al. ................. 514/5.4 |
| 7,232,892 | B2 * | 6/2007 | Goddard et al. ............ 530/388.8 |
| 7,294,690 | B2 * | 11/2007 | Goddard et al. ............... 530/350 |
| 7,411,048 | B2 * | 8/2008 | Kulaksiz et al. ............ 530/387.9 |
| 8,017,737 | B2 * | 9/2011 | Kulaksiz et al. ............ 530/387.9 |
| 8,487,081 | B2 * | 7/2013 | Vaulont et al. ............. 530/387.1 |
| 2010/0285027 | A1 * | 11/2010 | Vaulont et al. ............. 424/158.1 |

FOREIGN PATENT DOCUMENTS

| EP | 1392345 B1 | 4/2009 |
| WO | WO 9924594 A1 * | 5/1999 |
| WO | WO 0056879 A1 * | 9/2000 |
| WO | WO-02/098444 A2 | 12/2002 |
| WO | WO-2004/058044 A2 | 7/2004 |
| WO | WO 2006088972 A2 * | 8/2006 |
| WO | WO-2008/089795 A1 | 7/2008 |
| WO | WO-2008/097461 A2 | 8/2008 |
| WO | WO-2009/044284 A1 | 4/2009 |
| WO | WO-2010/065815 A2 | 6/2010 |

OTHER PUBLICATIONS

R. Gennaro et al. Biochim. Biophs. Acta (1998) 1425, pp. 361-368.*
BAF296 product sheet. R&D Systems. Mar. 12, 1997, 1 page.*
M. Ryle and J. Sage. J. Reprod. Fert. (1980) 60, pp. 243-245.*
AB-256-NA product sheet. R&D Systems. Jul. 8, 1997, 2 pages.*
http://en.wikipedia.org/wiki/Hepcidin#cite_note-pmid12663437-1.*
Nemeth et al., Blood, 101, 2461-3, 2003 (cited in Applicant's U.S. Pat. No. 8487081 at e.g. col. 2, lines 49-52).*
Pigeon et al. (Mar. 2001) A New Mouse Live-Specific Gene, Encoding a Protein Homologous to Human Antimicrobial Peptide Hepcidin, Is Overexpressed During Iron Overload, J. Biol. Chem. 276(11):7811-7819.
Park et al. (Mar. 2001) Hepcidin, A Urinary Antimicrobial Peptide Synthesized in the Liver, J. Biol. Chem. 276(11):7806-7810.
Krause et al. (Sep. 2000) LEAP-1, A Novel Highly Disulfide-bonded Human Peptide, Exhibits Antimicrobial Activity, FEBS Letters 480(2-3):147-150.
Nicolas et al. (Apr. 2002) Severe Iron Deficiency Anemia in Transgenic Mice Expressing Liver Hepcidin, Proc. Natl. Acad. Sci. USA 99(7):4596-4601.
Nicolas et al. (Jul. 2001) Lack of Hepcidin Gene Expression and Severe Tissue Iron Overload in Upstream Stimulatory Factor 2 (USF2) Knockout Mice, Proc. Natl. Acad. Sci. USA 98(15):8780-8785.
Fleming et al. (Jul. 2001) Hepcidin: A Putative Iron-Regulatory Hormone Relevant to Hereditary Hemochromatosis and the Anemia of Chronic Disease, Proc. Natl. Acad. Sci. USA 98(15):8160-8162.
Hemochromatosis, The Mayo Clinic, Sep. 14, 2004, pp. 1-7.
Anemia, The Mayo Clinic, Feb. 23, 2005, pp. 1-7.
Rivera et al. (Sep. 2005) Synthetic hepcidin causes rapid dose-dependent hypoferremia and is concentrated in ferroportin-containing organs, Blood 106(6):2196-2199.
Hemochromatosis [internet document] Updated Sep. 14, 2004, accessed Sep. 15, 2005, 10 pages <http://www.ohiohealth.com/healthreference/reference/992CA155-2D99-4C3E-BDBF4F4470FE5B8F.htm?category=disease>.
What is hemochromatosis? (2002) Cleve. Clin. J. Med. 69(3):238.
Type 1 diabetes, Updated Sep. 24, 2004, accessed Sep. 23, 2005, http://www.netdoctor.co.uk/diseases/facts/diabetesinsulindependent.htm, 4 pages.
Berlin, Hypertrophic Cardiomyopathy, http://www.healthopedia.com/hypertrophic-cardiomyopathy/prevent.html, reviewed Jul. 3, 2001, accessed Sep. 23, 2005, 1 page.
Rudinger (1976) Characteristic of the amino acids as components of a peptide hormone sequence, Peptide Hormones, Parsons, Ed. pp. 1-7.

(Continued)

*Primary Examiner* — Maury Audet
(74) *Attorney, Agent, or Firm* — Marshall, Gerstein & Borun LLP

(57) ABSTRACT

The invention concerns the use of hepcidin for the diagnosis and therapy of disorders of iron homeostasis. Hepcidin can be used in the treatment of disorders resulting from iron overload while inhibitors of hepcidin can be used in the treatment of anemia.

1 Claim, 7 Drawing Sheets

(56) References Cited

OTHER PUBLICATIONS

Voet et al. (1995) Section 9-3. Abnormal Hemogloblins, Biochemistry, 2nd Edition, pp. 235-241.
Smilek et al. (Nov. 1991) A single amino acid change in a myelin basic protein peptide confers the capacity to prevent rather than induce experimental autoimmune encephalomyelitis, Proc. Natl. Acad. Sci. USA 88:9633-9637.
Messer, Vasopressin and Oxytocin [web document] updated Apr. 3, 2000; http://www.neurosci.pharm.utoledo.edu/MBC3320/vasopressin.htm, 5 pages.
Notice of Opposition against European Patent No. 1392345 with Annex, Opponent: Eli Lilly and Company, dated Dec. 23, 2009.
Kulaksiz et al., Pro-hepcidin: Expression and cell specific localization in the liver and its regulation in hereditary haemochromatosis, chronic renal insufficiency, and renal anaemia. *Gut*, 53: 735-43 (2004).
Weiss et al., Serum hepcidin concentration in chronic haemodialysis patients: Associates and effects of dialysis, iron and erythropoietin therapy, *Eur. J. Clin. Invest.* 39(10): 883-90 (2009).
Kemna et al., Measuring serum hepcidin concentrations, *Nat. Clin. Prac. Gastroenterol. Hepatol.* 2: E1-2 (2005).
Roe et al., Serum prohepcidin concentration: No association with iron absorption in healthy men; and no relationship with iron status in men carrying HFE mutations, hereditary haemochromatosis patients undergoing phlebotomy treatment, or pregnant women, *Brit. J. Nutrition*, 97: 544-9 (2007).
Vallet et al., Glucose-dependent liver gene expression in upstream stimulatory factor 2-/- mice, 272(35): 21944-9 (1997).
Publication Timeline submitted in connection withe opposition against European Patent No. 1392345, dated Dec. 23, 2009.
Table from Figure 20 of WO-2008/089795 submitted in connection with opposition against European Patent No. 1392345, dated Dec. 23, 2009.
Declaration of Alfred Janetzko, Ph.D. submitted in connection with opposition against European Patent No. 1392345, dated Sep. 23, 2009.
Valore et al., Posttranslational processing of hepcidin in human hepatocytes is mediated by the prohormone convertase furin, *Blood Cells Molec. Dis.* 40: 132-8 (2008).
Kemna et al., Hepcidin: From discovery to differential diagnosis, *Prog. Hematol.* 93(1): 90-7 (2008).
Jordan et al., Hepcidin revisited, disulfide connectivity, dynamics, and structure, *J. Biol. Chem.* 284(36): 24155-67 (2009).
Kemna et al., Novel urine hepcidin assay by mass spectrometry, *Blood*, 106(9): 3268-70 (2005).
Anderson et al., Iron absorption and metabolism, *Curr. Opin. Gastroenterol.* 25: 129-35 (2009).
Nemeth et al., Hepcidin, a putative mediator of anemia of inflammation, is a type II acute-phase protein, *Blood*, 101(7): 2461-3 (2003).
Nemeth et al., IL-6 mediates hypoferremia of inflammation by inducing the synthesis of the iron regulatory hormone hepcidin, *J. Clin. Invest.*, 113(9): 1271-6 (2004).
Ganz et al., Hepcidin—A regulator of intestinal iron absorption and iron recycling by macrophages, *Best Prac. Res. Clin. Haematol.* 18(2): 171-82 (2005).
Ganz et al., Immunoassay for human serum hepcidin, *Blood*, 112(10): 4292-7 (2008).
Notice of Opposition against European Patent No. 1392345, Opponent: Dr. Hermann Gleiter, c/o Pfenning, Meinig & Partner GbR, dated Jan. 4, 2010.
Entry in Wikipedia related to "Iron overload" submitted in connection with opposition against European Patent No. 1392345, dated Jan. 4, 2010.
Entry in Wikipedia related to "Human iron metabolism" submitted in connection with opposition against European Patent No. 1392345, dated Jan. 4, 2010.
Nemeth et al., The N-terminus of hepcidin is essential for its interaction with ferroportin: Structure-function study, *Blood*, 107(1): 328-33 (2006).
Proprietor's response to Notices of Opposition, Eli Lilly and Company and Hermann Gleiter, dated Oct. 15, 2010.
Lesbordes-Brion et al., Targeted disruption of the hepcidin 1 gene results in severe hemochromatosis, *Blood*, 108(4): 1402-5 (2006).
Opponent, Hermann Gleiter, response to proprietor response of Oct. 15, 2010, dated Jan. 10, 2011.
Proprietors response to Opponent, Hermann Gleiter response of Jan. 11, 2011, dated Aug. 5, 2011.
Proprietors further written submission in connection with opposition against European Patent No. 1392345, dated Aug. 8, 2012.
Opponent, Hermann Gleiter, response to summons to attend oral proceedings, dated Aug. 9, 2012.
Opponent, Eli Lilly and Company, response to summons to attend oral proceedings, dated Aug. 9, 2012.
Proprietor's response to final submissions of opponents, dated Aug. 24, 2012.
Preza et al., Minihepcidins are rationally designed small peptides that mimic hepcidin activity in mice and may be useful for the treatment of iron overload, *J. Clin. Invest.* 121(12): 4880-8 (2011).
MacDougall et al., Current status of the measurement of blood hepcidin levels in chronic kidney disease, *Clin. J. Am. Soc. Nephrol.* 5: 1681-9 (2010).
Frazer et al., Hepcidin compared with prohepcidin: An absorbing story, *Am. J. Clin. Nutr.* 89: 475-6 (2009).
Transcript of an interview with Dr. Dorine Swinkels—Hepcidin in human iron disorders: Diagnostic implications, Clinical Chemistry, 2012.
Nicolas et al., Hepcidin, A new iron regulatory peptide, *Blood Cells Molec. Dis.* 29(3): 327-35 (2002).
Submission in opposition proceedings by Opponent: Eli Lilly and Company, Opposition against European Patent No. 1392345, dated Aug. 13, 2012.
Padlan et al., Anatomy of the antibody molecule, *Molec. Immunol.* 31(3): 169-217 (1994).
Edwards et al., The remarkable flexability of the human antibody repertoire: Isolation of over one thousand different antibodies to a single protein, BLyS, *J. Molec. Biol.* 334: 103-18 (2003).
Lottspeich et al. (Eds.), Bioanalytik, Chapter 36 (1998).
Alberts et al., Molecular Biology of the Cell, 3rd Edition (1994).
Majzoub et al., Molecular medicine knockout mice, *New Engl. J. Med.* 334(14): 904-7 (1996).
Haynes et al., Genetic manipulation of vascular adhesion molecules in mice, *J. Clin. Invest.* 98: 3192-5 (1996).
Minutes of oral proceedings before the opposition division, Opposition against European Patent No. 1392345, dated Oct. 9, 2012.
Interlocutory decision in opposition proceedings issued by European Patent Office, dated Dec. 6, 2012.
Statement of Grounds of Appeal by Opponent, Eli Lilly and Company, dated Apr. 16, 2013.
Declaration by Professor Dorine Swinkels submitted in connection with Statement of Grounds of Appeal by Opponent, Eli Lilly and Company, Apr. 16, 2013.
Statement of Grounds of Appeal by Opponent, Hermann Gleiter, dated Apr. 16, 2013.
Entry "to include" in Oxford Dictionary of English, 2nd Edition, submitted in connection with Grounds of Appeal by Opponent, Hermann Gleiter, dated Apr. 16, 2013.

* cited by examiner

Fig. 2
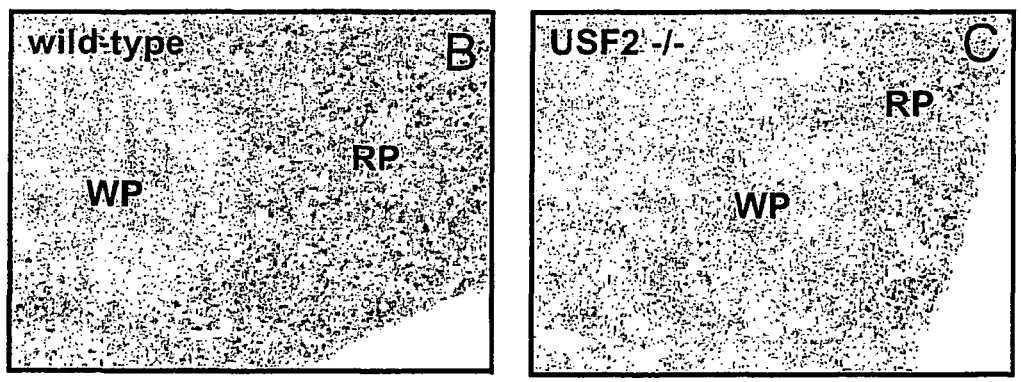

Fig 7    transgenic mice
A
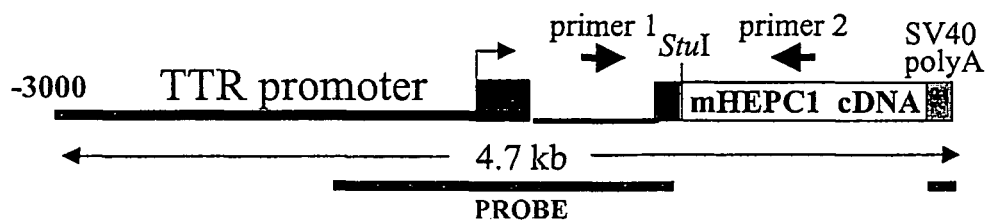
B
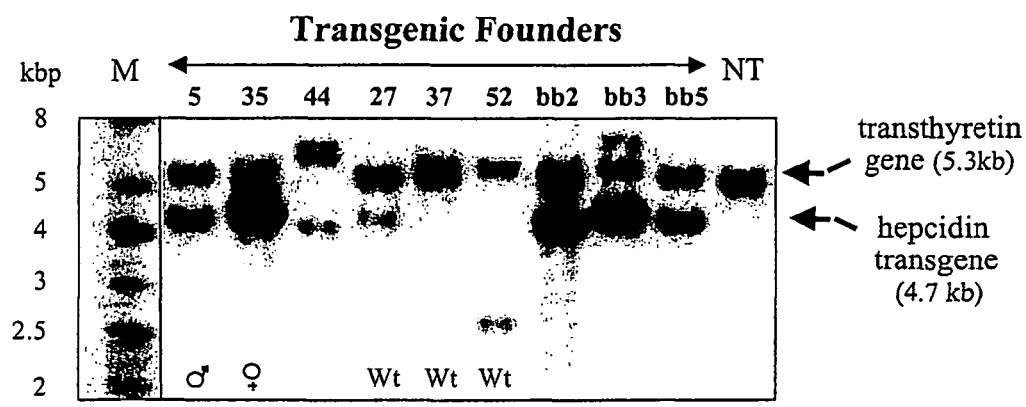

HEPCIDIN INHIBITORS FOR REGULATING IRON HOMEOSTASIS

This is a divisional application of U.S. application Ser. No. 10/478,987, filed Jul. 21, 2004 now U.S. Pat. No. 7,169,758, which is a U.S. National Phase Application of International Application No. PCT/EP02/06924, filed May 24, 2002, which claims the benefit of European Application No. 01401377.5, filed May 25, 2001, European Patent Application No. 01401537.4, filed Jun. 14, 2001, and European Patent Application No. 02290795.0, filed Mar. 29, 2002, all of which are herein incorporated by reference in their entirety.

JOINT RESEARCH AGREEMENT

INSERM (Institut National de la Sante et de la Recherche Medicale) and CNRS (Centre National de la Recherche Scientifique) are parties to a joint research agreement.

The invention relates to the diagnosis and therapy of disorders of iron homeostasis.

Iron is an essential element required for growth and survival of almost every organism. In mammals, the iron balance is primarily regulated at the level of duodenal absorption of dietary iron. Following absorption, ferric iron is loaded into apo-transferrin in the circulation and transported to the tissues, including erythroid precursors, where it is taken up by transferrin receptor-mediated endocytosis. Reticuloendothelial macrophages play a major role in the recycling of iron from the degradation of hemoglobin of senescent erythrocytes, while hepatocytes contain most of the iron stores of the organism in ferritin polymers. Over the past five years, an important body of information concerning the proteins involved in iron absorption and in the regulation of iron homeostasis has arisen from the study of inherited defects, both in humans and mice, leading to distinct iron disorders (for review see ANDREWS, Nat. Rev. Genet., 1, 208-217, 2000). In the case of iron deficiency, the pathophysiological consequences of gene defects identified are well understood since they usually result in loss of function of proteins directly involved in the pathway of iron absorption. The proteins include the iron transporters DMT1 (also called Nramp2 or DCT1) (FLEMING et al., Nat. Genet., 16, 383-386, 1997; GUNSHIN et al., Nature, 388, 482-488, 1997), ferroportin (also called IREG1 or MTP1) (DONOVAN et al., Nature, 403, 776-781, 2000), and copper oxidases coupled to ferroportin, namely ceruloplasmin (HARRIS, Proc. Natl. Acad. Sci. USA, 96, 10812-10817, 1999; YOSHIDA et al., Nat. Genet., 9, 267-272, 1995) and haephastin (VULPE et al., Nat. Genet., 21, 195-199, 1999).

In contrast, several abnormalities associated with genetic iron overload have identified various proteins whose functional role in the control of iron homeostasis remains poorly understood. In humans, hereditary hemochromatosis (HH) is a common autosomal recessive genetic disease caused by hyperabsorption of dietary iron leading to an iron overload in plasma and multiple organs, including in particular the pancreas, liver, and skin, and resulting in damages in these organs and tissues due to the iron deposits.

Hemochromatosis is usually due to a mutation in the HLA-linked hemochromatosis gene (named HFE) located on chromosome 6p, and most patients are homozygous for the C282Y mutation in HFE (FEDER et al., Nat. Genet., 13, 399-408, 1996). In addition, other loci have been involved in different HH families: a nonsense mutation in the transferrin receptor 2 gene (TFR2) on 7q has been reported in two HH non-HLA-linked families (CAMASCHELLA et al., Nat. Genet., 25, 14-15, 2000) and a locus for juvenile hemochromatosis has recently been mapped to chromosomal arm 1q (HFE2). Finally, although it has long been known that iron absorption is regulated in response to the level of body iron stores and to the amount of iron needed for erythropoiesis (ROY et al., FEBS Lett., 484, 271-274, 2000), the molecular nature of the signals that program the intestinal cells to adjust iron absorption still remains to be identified.

The disruption of the murine gene encoding the transcription factor USF2 and its consequences on glucose-dependent gene regulation in the liver (VALLET et al., J. Biol. Chem., 272, 21944-21949, 1997) have been recently reported.

BRIEF DESCRIPTION OF DRAWINGS

FIG. 1 (A) shows a liver section from 8-month-old wild-type mice (×50). FIG. 1 (B) shows a liver section from 8-month-old Usf2−/−littermate. FIG. 1(C) shows a liver section from 19-month-old Usf2−/− mouse (×10). The arrowheads in FIG. 1 (C) indicate iron in the nucleus of the hepatocyte. FIG. 1(D) shows a pancreas section in from a 8-month-old Usf2−/−mouse (×12.5). The arrowheads in FIG. 1 (D) indicate to islets of Langerhans scattered throughout the exocrine tissue. FIG. 1 (E) shows the levels of hepatic iron in mice as a function of age (in μg iron per gram of dry tissue). FIG. 1 (F) shows the levels of pancreatic iron (in μg iron per gram of dry tissue). In FIGS. 1 (E) and (F) measurements from wild-type and heterozygote mice are indicated by ▲ and measurements from Usf2−/−mice by □, respectively.

FIG. 2 shows that the spleen of Usf2−/−mice is resistant to natural iron deposition. FIG. 2 (A) shows age-dependent splenic non-heme iron concentration (micrograms of iron per gram dry tissue) as measured in control (wild-type and heterozygote mice, ▲) and Usf2−/−mice (□). FIGS. 2 (B) and (C) show spleen section from a representative 8-month-old wild-type mouse (×20) and a 8-month-old Usf2−/−littermate (×20), respectively, stained with the Perls' stain for iron. In FIGS. 2 (A) and (B), RP designates red pulp and WP designates white pulp.

FIG. 3 (A) shows a Northern blot measuring the expression levels of HFE and 18S in liver of Usf2−/−mice and wild-type (WT) mice. FIG. 3 (B) shows a Northern blot measuring the expression levels of TfR2 and 18S in liver of Usf2−/−mice and wild-type (WT) mice.

FIG. 4 is a schematic representation (not to scale) of the locus region encompassing the Usf2 and hepcidin genes. The targeted allele is represented with the betageo cassette insertion in exon 7. On the right of FIG. 4 is a Southern blot from tail DNA of wild-type, heterozygote and homozygote mice.

FIG. 5 (A) shows a Northern Blot of total liver RNAs from wild-type, Usf2+/− and Usf2−/−hybridized with a 32P-labeled HEPC probe which most likely recognized both HEPC1 and HEPC2 transcripts. FIGS. 5 (B) and (C) show RT-PCR measurement of HEPC1 and HEPC2 levels, respectively.

FIG. 7 shows characteristics of TTR-hepc1 transgenic mice. FIG. 7 (A) shows a schematic representation of the TTR-hepC1 construction. FIG. 7 (B) shows a Southern blot with the different founders.

Figure 1:
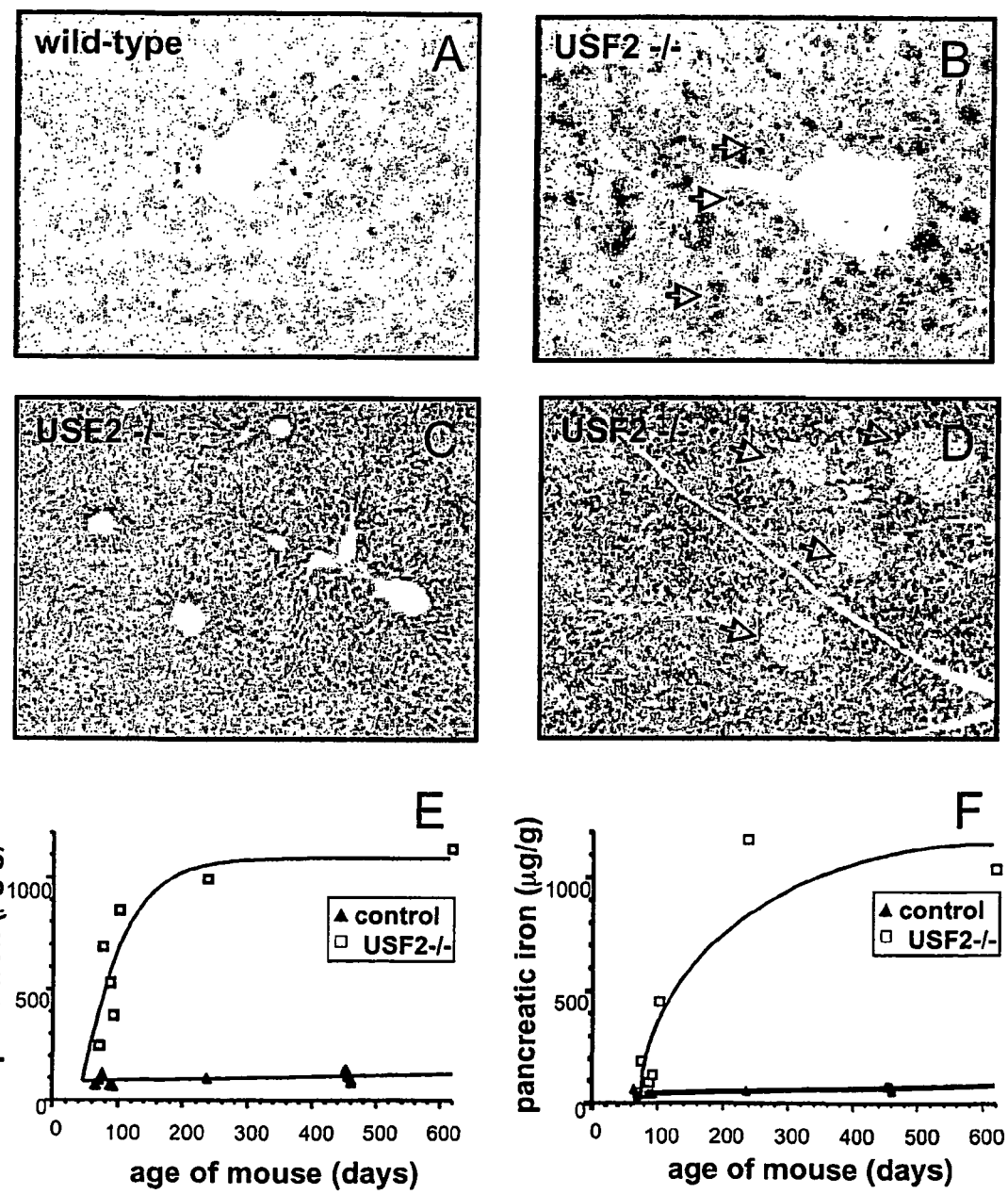
FIG. 1 shows the effects of massive iron overload in the liver and pancreas of Usf2−/−mice.

The inventors have now observed that, surprisingly, Usf2−/−mice develop multivisceral iron overload that spares only the spleen whose iron content is strikingly lower in knockout animals than in controls. These iron metabolic disorders resemble those observed in hereditary hemochromatosis. However, no alteration in genes previously identified for their implication in this pathology, e.g., HFE or TFR2 was observed. Thus the inventors searched for new candidate genes that may account for the abnormalities of iron homeostasis in Usf2−/−mice by suppressive subtractive hybridization between livers from Usf2−/−mice and wild-type mice. This allowed to isolate a cDNA encoding the peptide hepcidin.

Hepcidin (also referred as LEAP-1, for liver-expressed antimicrobial peptide) was recently purified from human blood ultrafiltrate and from urine and was found to be a disulfide-bonded peptide exhibiting antimicrobial activity (KRAUSE et al., FEBS Lett., 480, 147-150, 2000; PARK et al., J. Biol. Chem., 276, 7806-7810, 2001). The protein is synthesized in the liver in the form of a propeptide that contains 83 aminoacids and is converted into mature peptides of 20, 22 or 25 aminoacids (PARK et al., J. Biol. Chem., 276, 7806-7810, 2001; PIGEON et al., J. Biol. Chem., 276, 7811-7819, 2001). Hepcidin was also recently reported to be highly synthesized in livers of experimentally or spontaneously iron overloaded mice (PIGEON et al., J. Biol. Chem., 276, 7811-7819, 2001). Although the relationship of this overexpression with iron overload was questioned, it was indicated that it probably resulted from inflammation related to chronic iron overload.

In contrast, the Inventors have now shown that a complete defect in hepcidin expression leads to a progressive tissue iron overload in Usf2−/−mice. Further they have obtained transgenic mice having a transgene expressing hepcidin under control of a constitutive liver-specific promoter, and have observed that said transgenic mice were severely anemic.

These findings allow to propose new means of regulation of iron homeostasis, in particular through regulation of dietary iron capture by the intestin, or of maternofoetal iron transport through the placental barrier, and of iron recycling by reticuloendothelial macrophages.

Accordingly, the present invention proposes the use of a polypeptide comprising a sequence of 20 amino acids having cysteine residues at positions 2, 5, 6, 8, 9, 14, 17, and 18, and at least 50% identity or 60% similarity, preferably at least 60% identity or at least 70% similarity, with the following sequence:
Ile Cys Ile Phe Cys Cys Gly Cys Cys His Arg Ser Lys Cys Gly Met Cys Cys Lys Thr (SEQ ID NO: 1)
or the use of a nucleic acid encoding said polypeptide, for preparing a medicament useful for reducing iron overload.

Preferred polypeptides or nucleic acids for use according to the invention are the mature forms of human hepcidin, represented for instance by a polypeptide of 20 amino-acids having the sequence SEQ ID NO: 1, or by a polypeptide of 22 amino-acids having the sequence:

```
Phe Pro Ile Cys Ile Phe Cys Cys Gly   (SEQ ID NO: 2)
Cys Cys His Arg Ser Lys Cys Gly Met
Cys Cys Lys Thr,
``` or by a polypeptide of 25 amino-acids having the sequence:

```
Asp Thr His Phe Pro Ile Cys Ile Phe   (SEQ ID NO: 3)
Cys Cys Gly Cys Cys His Arg Ser Lys
Cys Gly Met Cys Cys Lys Thr,
``` or nucleic acids encoding said polypeptides.

Precursors of said mature forms of hepcidin, i.e. prohepcidin and preprohepcidin and nucleic acids encoding said precursors can also be used.

Other examples of polypeptides or nucleic acids suitable for use according to the invention are vertebrate, preferably mammalian, homologous of mature forms of human hepcidin or precursors thereof, or nucleic acids encoding said polypeptides. Known vertebrate homologous of human hepcidin include for instance rat hepcidin, mouse hepcidin, trout hepcidin.

Chimeric polypeptides, comprising the sequence of a mature form of hepcidin, (and eventually, all of part of the pro- or the prepro-sequence can also be used.

The invention also encompasses the use of functional equivalents of the above-defined polypeptides. Functional equivalents are herein defined as peptide variants, or other compounds having the same functional activity as the mature forms of hepcidin. Examples of such functional equivalents include chemical compounds which are modeled to mimic the three dimensional structure of any of the polypeptides having the sequence SEQ ID NO: 1, SEQ ID NO: 2, or SEQ ID NO: 3. Of particular interest are derivatives of said polypeptides having an improved stability and biological half life. Classical examples of such derivatives are for instance "retro-inverso" peptides, wherein the sequence of the amino-acids is reversed, and the L-amino acids are replaced with D-amino acids.

All these polypeptides and nucleic acids can be obtained by classical methods known in themselves. For instance, the 20 amino-acids and 25 amino-acids forms of hepcidin can be obtained from plasma or from urine, as disclosed by KRAUSE et al. or PARK et al. Alternatively, they can be obtained by culturing cells expressing hepcidin, and recovering said polypeptide from the cell culture.

According to a particular embodiment, said cells are host cells transformed by a nucleic acid encoding one of the polypeptides defined above.

Chemical synthesis can also be used, in particular in the case of the peptide derivatives.

A nucleic acid encoding hepcidin can for instance be obtained from a genomic or cDNA library of a vertebrate, using suitable primers able to hybridize selectively with said nucleic acids. It can also be obtained by the classical techniques of polynucleotide synthesis.

The present invention also provides methods for screening functional equivalents of hepcidin able to reduce iron absorption.

By way of example, functional equivalents having the biological properties of hepcidin in regulating iron homeostasis can easily be screened with animals, in particular non-human mammals, lacking hepcidin, for instance knockout mice having a defect in hepcidin expression resulting in an iron overload.

In particular, a method for screening functional equivalents of hepcidin able to reduce iron absorption comprises the following steps:
administering to a knockout animal defective in hepcidin expression a compound to be tested for its ability to reduce iron absorption;

determining the effect of said compound on iron overload in said animal.

Medicaments obtained according to the invention are useful for preventing and/or treating:

all forms of hemochromatosis;

secondary iron overload, related for instance to hereditary and/or congenital anemias such as thalassemia;

and diseases associated therewith. These latter diseases include for instance hepatocarcinoma, cardiomyopathy, or diabetes.

According to another aspect, the invention also proposes the use of an inhibitor of the expression of hepcidin or of the activity of hepcidin for preparing a medicament useful for increasing iron absorption through the increase of dietary iron capture by the intestine, and/or the increase of iron recycling by the macrophages. Said medicament is useful for treating anemia or anemia related diseases. This includes in particular anemia associated with acute or chronic diseases occurring under conditions such as infection or inflammation, for instance osteoarticular diseases such as rheumatoid polyarthritis, or malignacies, especially when associated with an inflammatory syndrome.

Inhibitors of the expression of hepcidin include for instance antisense RNA or DNA molecules, or ribozymes.

Inhibitors of the activity of hepcidin include for instance anti-hepcidin antibodies, in particular antibodies directed against the mature forms of hepcidin.

The present invention also provides methods for screening other inhibitors of the activity of hepcidin, for instance with transgenic animals, in particular transgenic non-human mammals such as transgenic mice having a transgene expressing hepcidin, said expression inducing anemia in said animal.

For instance, a method for screening inhibitors of the activity of hepcidin able to increase iron absorption comprises the following steps:

administering to a transgenic animal having a transgene expressing hepcidin a compound to be tested for its ability to increase iron absorption through the inhibition of the activity of hepcidin;

determining the effect of said compound on anemia in said animal.

The medicaments obtained according to the invention can be administered in various ways, depending on their nature:

For instance, hepcidin polypeptides or functional equivalents thereof, as well as hepcidin inhibitors such as anti-hepcidin antibodies can be administered by themselves, or mixed with suitable carriers or excipient(s). They can be used systemically or locally. A preferred route of administration is the parenteral route, including for instance intramuscular, subcutaneous, intravenous, or intraperitoneal injections.

The oral route can also be used, provided that the medicament is in a form suitable for oral administration, able to protect the active principle from the gastric and intestinal enzymes.

As indicated above, one can also use a nucleic acid molecule, for instance a nucleic acid encoding any of the hepcidin polypeptides mentioned above, in order to enable the expression of said polypeptide in the cells of or a nucleic acid transcribed into an antisense RNA, in order to suppress the expression of hepcidin in the cells of a subject to be treated.

In this case, said nucleic acid molecule is introduced into the target cells by the classical techniques of gene transfer.

Typically, said nucleic acid molecule is placed under transcriptional control of an appropriate promoter. The choice of the promoter depends on the intended use of the medicament, and/or on the target organ or tissue. Thus one can chose a promoter either constitutive or inductible and/or either ubiquitous or tissue-specific.

The expression cassette thus obtained can be directly transferred in the cells as naked DNA, or placed in an appropriate vector, such as a viral vector, for instance an adenovirus derived vector.

The choice of the method of transfer and/or of the vector depends on the target organ or tissue, and/or on whether a short-time expression (transient expression) or stable expression is wanted.

Gene transfer can be performed ex vivo on cells removed from the subject to be treated and thereafter re-implanted into said subject, or can be performed by direct administration of the nucleic acid to said subject.

The invention also provides genetically modified non-human animals, wherein the genetic modification results in an anomaly in hepcidin expression. The invention also encompasses biological material, such as cells, tissues and organs obtained from said genetically modified animals.

This comprises in particular knockout animals, preferably knockout mammals, and in particular knockout mice expressing no functional hepcidin. This lack of expression of hepcidin induces an iron overload in said animals. The known knockout mices, disclosed by VALLET et al. (J. Biol. Chem., 272, 21944-21949, 1997) wherein the gene encoding the transcription factor USF2 is inactivated, are excluded.

Knockout animals of the invention are obtainable by total or partial inactivation of the gene(s) of hepcidin, said inactivation resulting in the absence of production of hepcidin, or in a loss of functionality thereof.

The inactivation of the gene of hepcidin may target:

the sequence encoding hepcidin, resulting in the absence of production of said protein, or in a loss of functionality thereof, and/or at least one of the regulatory sequences controlling the expression of hepcidin, resulting in a lack of production of hepcidin, or in a drastic decrease in the amount of hepcidin produced.

Other genetically modified animals of the invention having an anomaly in hepcidin expression are transgenic animals, preferably transgenic mammals, and in particular transgenic mice, having a transgene expressing hepcidin, said expression resulting in anemia in said animals.

Suitable methods for the preparation of transgenic or knockout animals are well-known in the art, for instance disclosed in: *Manipulating the Mouse Embryo*, $2^{nd}$ Ed., by HOGAN et al., Cold Spring Harbor Laboratory Press, 1994; *Transgenic Animal Technology*, edited by C. PINKERT, Academic Press Inc., 1994; *Gene Targeting: A Practical Approach*, edited by A. L. JOYNER, Oxford University Press, 1995; *Strategies in Transgenic Animal Science*, edited y G. M. MONASTERSKY and J. M. ROBL, ASM Press, 1995; *Mouse Genetics: Concepts and Applications*, by Lee M. SILVER, Oxford University Press, 1995.

The knockout animals expressing no functional hepcidin, as well as transgenic animals having a transgene expressing hepcidin, can be used as models for studying the mechanisms of iron homeostasis. They can also be used, as described above, for screening of compounds having the same effect as hepcidin on iron absorption, or for screening of compounds able to inhibit the effect of hepcidin on iron absorption.

The invention also provides diagnostic methods for determining whether an anomaly of iron absorption is associated with a mutation in hepcidin or with an abnormal hepcidin production.

For instance the invention provides:
a method for detecting whether an anomaly of iron absorption results from an abnormal hepcidin production, wherein said method comprises determining the quantity of hepcidin in a biological sample from a subject suffering from said anomaly;
a method for detecting whether an anomaly of iron absorption is associated with a mutation impairing the production of functional hepcidin, wherein said method comprises detecting a mutation in the gene of hepcidin in a nucleic acid sample obtained from a subject suffering from said anomaly.

Biological samples suitable for determining the quantity of hepcidin include for instance blood, urine, or amniotic fluid samples, or organ biopsies, in particular liver biopsies or placenta biopsies.

Nucleic acid samples suitable for detecting a mutation impairing the production of functional hepcidin include RNA, cDNA or genomic DNA.

The amount of hepcidin in a biological sample can easily be determined by well-known methods, such as, by way of example, HPLC chromatography, mass spectroscopy, or by immunoassay using anti-hepcidin antibodies.

Mutations in the gene of hepcidin can easily be detected by sequencing said gene or a part thereof, previously isolated from the DNA sample to be tested, and comparing the sequence with the corresponding wild-type sequence(s), obtainable of one or several subjects having no anomaly of iron homeostasis.

The present invention will be further illustrated by the additional description which follows, which refers to examples illustrating the effects of the lack of production of hepcidin in knockout animals or of overproduction of hepcidin in transgenic animals. It should be understood however that these examples are given only by way of illustration of the invention and do not constitute in any way a limitation thereof.

EXAMPLE 1

Characteristics of Knockout Mice Deficient in Hepcidin Expression

Materials and Methods
Generation and Genotyping of Usf2−/−Mice

Disruption of the Usf2 gene has been previously described (VALLET et al., J. Biol. Chem., 272, 21944-21949, 1997). The mutated allele contains the promoterless IRESβgeo cassette in exon 7 of the murine USF2 gene. All studied mice have a mixed genetic background that included contributions from C57BL/6 and 129/Sv strains. Mice were maintained on a standard laboratory mouse chow (AO3, UAR, France) containing 280 mg of ferric carbonate per kg. Mice were sacrificed from the ages of 2.5 months up to 19 months. Genotyping on mouse-tail DNA was performed using a single PCR reaction in order to identify wild-type (WT) and USF2 knockout alleles. Genomic DNA (0.5-1 µg) was used in a 50 µl reaction that included 3 primers: the wild-type USF2 allele was amplified using the following primers:

```
forward (annealing in intron 6):
GCGAAGCCCTGGGTTCAATC           (SEQ ID NO: 4)
and reverse (annealing in intron 7):
GGGGTCCACCACTTCAAGAGG.         (SEQ ID NO: 5)
```

The knockout USF2 allele was amplified using the following primers:

```
forward:
GCGAAGCCCTGGGTTCAATC,          (SEQ ID NO: 6)
and reverse (annealing in the Neo
selection marker of the
targeting construct):
GAATTCTCTAGAGCGGCCGGAC.        (SEQ ID NO: 7)
```

PCR was performed as follows: 37 cycles (each cycle consisting of 30 s at 94° C., 30 s at 56° C. and 40 s at 72° C.) with an initial denaturation step at 94° C. for 4 min, and a final elongation step at 72° C. for 5 min in 20 mM Tris-HCl (pH 8.4), 50 mM KCl, 0.05% W-I, 2 mM $MgCl_2$, 5% glycerol, 0.04% bromophenol blue, 0.2 mM each dNTP, 0.2 µM each primer, 2 units of Taq polymerase (Gibco). The reaction was analyzed on 1.5-2% agarose gel containing ethidium bromide. This PCR method for mouse genotyping was found to give the same results as the Southern blot method previously reported (VALLET et al., J. Biol. Chem., 272, 21944-21949, 1997).

Generation of a Subtracted Library by Suppression Substractive Hybridization (SSH)

Total RNA was prepared as previously described (CHOMCZYNSKI and SACCHI, Anal. Biochem., 162, 156-159, 1987). Polyadenylated RNA was isolated using oligo (dT) cellulose (Boehringer Mannheim Biochemica). SSH was performed between 3 pooled liver RNA from 5-month-old homozygous USF2 deficient mice ('driver') and liver RNA from a 5-month-old wild-type mouse ('tester') using the PCR-Select™ cDNA subtraction kit (Clontech) according to the manufacturer's recommendations for all steps. Briefly 14 ng of the ligated tester and 420 ng of non-ligated driver cDNAs were mixed, denatured and allowed to re-anneal. After subtractive hybridization, 1 µl of cDNA was amplified by two rounds of PCR. The subtracted cDNA library was cloned into the pT-Adv vector using the AdvanTAge™ PCR cloning kit (Clontech). After the secondary PCR (15 cycles) with the Advantage cDNA polymerase mix (Clontech), the subtracted PCR cDNA mix was incubated for a further 10 min at 72° C. with 1 unit Taq DNA polymerase (Gibco BRL) to maximize the cloning efficiency and purified with the QIAquick PCR purification kit (Qiagen). The ligation mixture was introduced into the Electromax bacterial strain DH10B (Gibco BRL) by electroporation (1.8 kV) using a Cell-Porator® (Gibco BRL). The library was plated onto 22×22 cm agar plates containing ampicillin (100 µg/ml) and spread with 40 µl X-gal (40 mg/ml) and 40 µl IPTG (0.1 M). Bacteria were grown at 37° C. until colonies were visible and kept at 4° C. until blue/white staining could be clearly distinguished.

Reverse Northern High Density Blots and Screening

A total of 400 individual clones were collected, resuspended into 30 µl of water, heated at 100° C. for 10 min, then placed in ice for 5 min and centrifuged for 5 min. PCR was performed using 3 µl of clear supernatant with the following primers:

```
forward:
5'-CAGGAAACAGCTATGACCATGATTAC-3',   (SEQ ID NO: 8)
and reverse:
5'-TAATACGACTCACTATAGGGCGA-3'.      (SEQ ID NO: 9)
```

The PCR products were blotted onto Hybond-N+ filters (Amersham Pharmacia). Blots were hybridized overnight at 72° C. with $^{32}$P-dCTP-labelled double-stranded cDNA (RTS RadPrime DNA Labeling System, Gibco) synthesized with 2 µg polyadenylated RNA from wild-type or Usf2–/–mouse liver, as described below. Blots were washed four times in 2×SSC/0.1% SDS at 68° C. for 20 min and two times in 0.2×SSC/0.1% SDS at 68° C. for 20 min.

Reverse Transcription and RT-PCR

Double-stranded cDNA was synthesized in 20 µl, with 2 µg total RNA (or polyA RNA for the subtracted library), in the presence of 0.25 mM of each dNTP, 200 ng of random hexanucleotide primers, 20 units RNAsin (Promega), 10 mM DTT and 200 units M-MLV reverse transcriptase (Gibco). After denaturation of RNA at 70° C. for 10 min in a therman cycler (Perkin Elmer Cetus), the reaction was performed for 1 hour at 42° C. before reverse transcriptase was inactivated for 6 min at 96° C. At the end of the reaction 80 µl of 10 mM Tris-HCl (pH 8.0) and 0.1 mM EDTA (pH 8.0) were added. PCR amplification was performed with 5 µl reverse transcriptase reaction mixture in 50 µl 20 mM Tris-HCl (pH 8.4), 50 mM KCl, 2 mM MgCl$_2$, 0.05% (v/v) W–1, 0.2 mM of each dNTP, 1 pmol of forward and reverse specific primers (listed below), 1 pmol of forward and reverse control β-actin primers and 2 units of Taq polymerase (Gibco). PCR conditions were 25 cycles of denaturation at 94° C. for 20 s, annealing at 50° C. for 20 s and primer extension at 72° C. for 20 s. Following PCR, the amplified products (171 bp for HEPC1 or HEPC2 and 250 bp for β-actin) were separated by electrophoresis on 1.5% agarose gel.

Sequences of the primers were as follows:

```
* HEPC1:
forward:
5'-CCTATCTCCATCAACAGATG-3'    (SEQ ID NO: 10)
and reverse
5'-AACAGATACCACACTGGGAA-3';   (SEQ ID NO: 11)

* HEPC2:
forward:
5'-CCTATCTCCAGCAACAGATG-3'    (SEQ ID NO: 12)
and reverse:
5'-AACAGATACCACAGGAGGGT-3';   (SEQ ID NO: 13)

* β-actin:
forward:
5'-AGCCATGTACGTAGCCATCC-3'    (SEQ ID NO: 14)
and reverse:
5'-TTTGATGTCACGCACGATTT-3'.   (SEQ ID NO: 15)
```

The primers used for amplification of DMT1 were as follows:

```
* DMT1 isoform without IRE:
forward:
5'-TCCTGGACTGTGGACGCT-3'      (SEQ ID NO: 16)
and reverse:
5'-GGTGTTCAGAAGATAGAGTTCAGG-3'; (SEQ ID NO: 17)

* DMT1 with IRE:
forward:
5'-TGTTTGATTGCATTGGGTCTG-3'   (SEQ ID NO: 18)
and reverse:
5'-CGCTCAGCAGGACTTTCGAG-3';   (SEQ ID NO: 19)

* Normalization with 14S:
forward:
5'-CAGGACCAAGACCCCTGGA-3'     (SEQ ID NO: 20)
and reverse:
5'-ATCTTCATCCCAGAGCGA-3'      (SEQ ID NO: 21)
```

Northern Blot

The primers used for amplification of probes used to detect specific mRNAs were:

```
* for mouse hemochromatosis (HFE) cDNA
amplification (1080 bp):
forward:
5'-ATGAGCCTATCAGCTGGGCT-3'    (SEQ ID NO: 22)
and reverse:
5'-TCACTCACAGTCTGTTAAGA-3';   (SEQ ID NO: 23)

* for mouse transferrin receptor (TfR)
cDNA amplification (285 bp):
forward:
5'-GAAATCCCTGTCTGTTATAC-3'    (SEQ ID NO: 24)
and reverse:
5'-GGCAAAGCTGAAAGCATTTC-3';   (SEQ ID NO: 25)

* for mouse transferrin receptor 2 (TFR2)
cDNA amplification (333 bp):
forward:
5'-TACAGCTCGGAGCGGAACG-3'     (SEQ ID NO: 26)
and reverse:
5'-TTACAATCTCAGGCACCTCC-3';   (SEQ ID NO: 27)

* for mouse ceruloplasmin cDNA
amplification (350 bp):
forward
5'-ACTTATTTCAGTTGACACGG-3'    (SEQ ID NO: 28)
and reverse
5'-GCAGCACATACACATACTGT-3';   (SEQ ID NO : 29)

* for mouse heme oxygenase 1 (Hmox1)
cDNA amplification (258 bp):
forward:
5'-ATGGAGCGTCCACAGCCCG-3'     (SEQ ID NO: 30)
and reverse:
5'-CCTTCGGTGCAGCTCCTCAG-3'.   (SEQ ID NO: 31)
``` gel (QIAquick PCR purification kit, Qiagen) and subcloned into TA vector (AdvanTAge cloning kit, Clontech). Recombinant plasmid was selected according to the protocol and amplified into LB medium containing 100 µg/ml ampicillin and purified (QIAprep Spin Miniprep, Qiagen). Each cDNA was purified from the vector after EcoRI digestion and migration on agarose gel. The probe used to detect HEPC1 mRNA was prepared from the EcoRI digestion of the pT-Adv/HEPC1 isolated by suppressive subtractive hybridization. Twenty micrograms of RNA from each source was denatured in formaldehyde-containing buffer and electrophoresed in 1% agarose, 2.2 M formaldehyde gels. Northern blot was performed as previously described (VALLET et al., J. Biol. Chem., 272, 21944-21949, 1997). Each blot was stripped and reprobed with ribosomal 18 S cDNA, to check for the integrity and the amount of loaded RNAs.

Southern Blot

Southern blots were performed as previously described (VALLET et al., J. Biol. Chem., 272, 21944-21949, 1997). The HEPC1 probe was prepared from a 1437 bp mouse genomic DNA fragment amplified with the following primers:

```
forward:
5'-GAGCAGCACCACCTATCTCCA-3'     (SEQ ID NO: 32)
and reverse:
5'-AACAGATACCACAGGAGGGT-3'.     (SEQ ID NO: 33)
```

After digestion with PvuII, a 545 bp fragment was purified from agarose gel and used as probe for Southern blot. This HEPC1 probe showed 95% identity with the homologous HEPC2 region.

Hematological Analysis of Mice

Blood was obtained by retroorbital phlebotomy before sacrifice of mice and collected in heparinized tubes (Capiject™ T-MLH, Terumo® medical corporation). Blood cell counts and erythrocyte parameters were determined using a MaxM coulter automatic analyzer.

Iron Measurements and Histology

Quantification of iron level was performed as previously described by Torrance and Bothwell (1968) on fragments or total organs using IL Test™ (Instrumentation Laboratory). For histology, tissues were fixed in 4% formaldehyde, embedded in paraffin, mounted onto slides and stained with Prussian blue and nuclear red counterstain using standard procedures.

Results

Massive Iron Overload in Liver and Pancreas of Usf2−/− Mice

All USF2−/−mice exhibit after the third month of life a dense brown pigmentation of the liver and a more or less pronounced bronze pigmentation of the pancreas. As this phenotypic trait is characteristic of hemochromatosis, the inherited disorder of iron absorption, we decided to analyze the iron status of the Usf2−/−mice. First, to assess the level of iron accumulation, Perls' Prussian blue staining was performed on liver and pancreas of wild-type and Usf2−/−mice maintained on a standard diet.

The results are shown in FIG. 1 (A to D):

Legend: Liver section from (A) 8-month-old wild-type mice (×50), (B) 8-month-old Usf2−/−littermate and (C) 19-month-old Usf2−/−mouse (×10). Pancreas section in (D) is from a 8-month-old Usf2−/−mouse (×12.5). Arrowheads in C indicate iron in the nucleus of the hepatocyte. Arrowheads in D point to islets of Langerhans scattered throughout the exocrine tissue.

While control mice showed very little or no positive iron staining in the liver (FIG. 1A), Usf2−/− mice displayed iron accumulation in hepatocytes (FIG. 1B-C) This iron deposition was primarily confined to periportal hepatocytes, and then, with age, the number of stained hepatocytes increased. By 19 months of age, as shown in FIG. 1C, iron accumulation was considerable and the staining was homogeneous throughout the liver parenchyma. Furthermore, a strong nuclear iron accumulation was detected in some hepatocytes (FIG. 1B). For the pancreas, similar results were obtained i.e. no staining in the control tissue and a strong iron accumulation in the exocrine pancreas of Usf2−/−mice (FIG. 1D).

To quantify more accurately the iron overload during the life of animals, iron levels were measured in liver and pancreas of mice from 2.5 to 19 months of age.

The results are shown in FIG. 1 (E and F):

Legend: Age-dependent hepatic (E) and pancreatic (F) non-heme iron concentration (micrograms of iron per gram dry tissue) as measured in control (wild-type and heterozygote mice, ▲) and Usf2−/−mice (□).

As shown in FIG. 1E, iron accumulated in the liver of mice between 60 and 100 days after birth and reached a plateau corresponding approximately to a 10-fold greater iron content than in wild-type mice. In the pancreas (FIG. 1F), iron accumulation was more progressive, with levels in Usf2−/− mice a maximum of 20-fold higher than in wild-type mice. Iron accumulation was also measured in kidney and heart showing a 2- and 4-fold accumulation, respectively. Finally, a 1.7-fold higher iron level was found in serum of Usf2−/− compared to control mice (3.550±259 µg of iron/l in controls [n=15] vs 6.274±514 µg of iron/l in Usf2−/−mice [n=13] P<0.0001), but this increase did not appear to be age-dependent. This increase in serum iron level in Usf2−/−mice was correlated with a 1.6-fold increase in transferrin saturation (61±9% saturation in controls [n=6] vs 95±9% saturation in Usf2−/−mice [n=6] P<0.0004). Finally, in the oldest female analyzed so far (19 months), the iron overload became widespread with increased iron level in all tissues tested including muscle, uterus, lung and pituitary gland (not shown).

The Spleen of Usf2−/−Mice is Resistant to Natural Iron Deposition

The results are shown in FIG. 2:

Legend of FIG. 2:

(A) Age-dependent splenic non-heme iron concentration (micrograms of iron per gram dry tissue) as measured in control (wild-type and heterozygote mice, ▲) and Usf2−/− mice (□). Spleen section from a representative (B) 8-month-old wild-type mouse (×20) and (C) a 8-month-old Usf2−/− littermate (×20) stained with the Perls' stain for iron. RP, red pulp; WP white pulp.

In contrast to all other tissues tested, an age-dependent iron accumulation was observed in the spleen of wild-type mice, as shown (FIG. 2A).

Granules which gave a positive reaction with Perls' Prussian blue staining were observed, primarily scattered between cells of the red pulp (FIG. 2B). We found this accumulation to fluctuate greatly between mice, suggesting that it may depend on the (129/Sv×C57BL/6) hybrid strain background of each animal. This natural iron storage has been previously reported in C57BL/6 mice and was described to occur mainly in splenic macrophages (VENINGA et al., Lab. Anim., 23, 16-20, 1989). Surprisingly, in spleen of Usf2−/−mice, iron levels remained very low (FIG. 2A), with a complete absence of Perls' Prussian blue staining (FIG. 2C).

Erythroid Parameters are not Affected in Usf2−/−Mice

To rule out the possibility that the increased iron accumulation in Usf2−/−mice might result from dyserythropoietic anemia, erythroid parameters in control and Usf2−/−mice at different ages were measured. Values of red blood cell count (RBC, $10^6$/ml), hemoglobin concentration (Hb, g/dl) and mean corpuscular volume (MCB, fl) were normal: RBC, Hb and MCB of 10.3±0.3, 16.73±0.49 and 48.27±0.67 for wild-type mice (n=3); 10.0±0.3, 15.67±0.06 and 48.63±1.36 for Usf2−/−mice (n=3), respectively.

Thus, interestingly, the iron abnormalities observed in Usf2−/−mice, including the resistance of spleen to iron accumulation and normal hematological parameters, strikingly resemble the phenotype of HFE−/−mice (LEVY et al., Blood, 94, 9-11, 1999; ZHOU et al., Proc. Natl. Acad. Sci. USA, 95, 2492-2497, 1998), the murine model of hereditary hemochromatosis.

Expression of HFE and TFR2 Genes is not Modified in the Liver of Usf2−/−Mice

Because USF2 is a transcription factor, it was determined whether USF2 could be involved in the regulation of genes encoding proteins related to iron metabolism. Due to the similarity between HFE−/−mice and Usf2−/−model, the expression of the HFE gene was first checked. The gene encoding transferrin receptor-2, a mutation of which was recently reported in HH (CAMASCHELLA et al., Nat. Genet., 25, 14-15, 2000) was also looked at.

Figure 3:
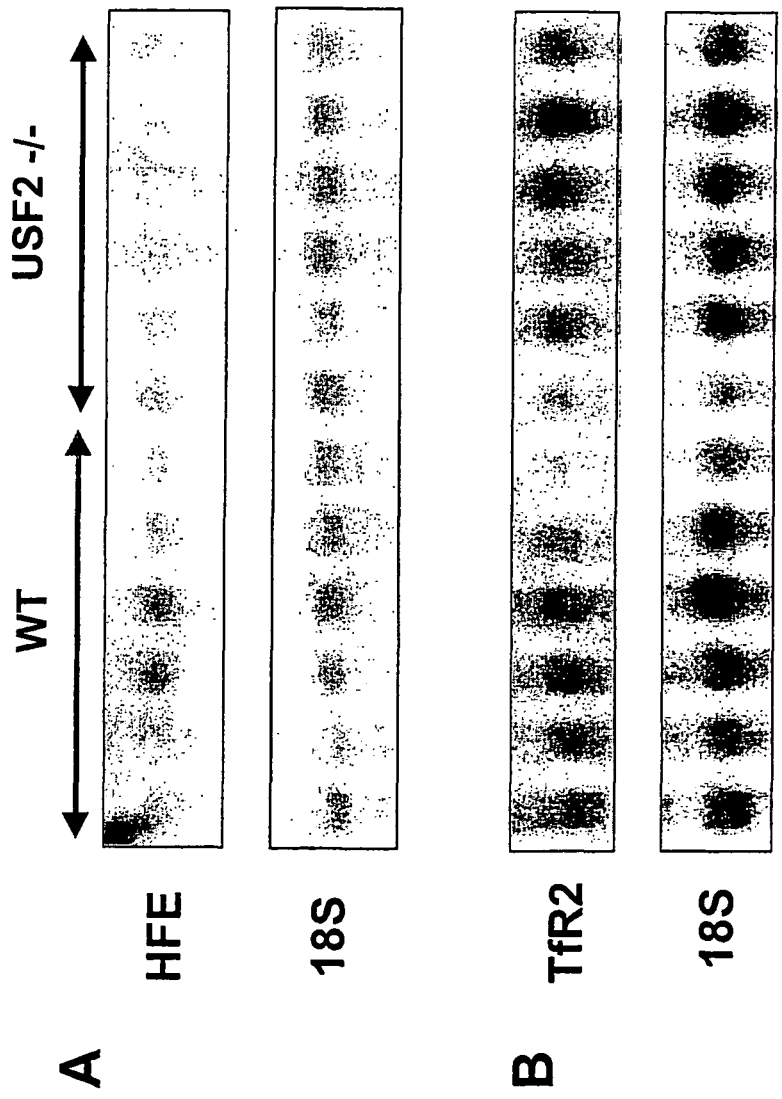
FIG. 3 compares the levels of expression of HFE and TFR2 genes in the liver of Usf2−/−mice and wild-type mice.

The results are shown in FIG. 3.

Legend of FIG. 3:

Twenty micrograms of total liver RNAs from wild-type mice and Usf2−/−mice (from 3 toll months old) were electrophoresed and blotted. Blots were hybridized with a 32P-labeled probe (made by PCR, as described in Materials and Methods) for HFE (A) and RTf2 (B).

As shown in the Northern blot of FIG. 3A, abundance of HFE mRNA in liver of Usf2−/−mice is comparable to that of wild-type mice. Northern blot analysis also demonstrated that the hepatic expression of the gene RTf2 was not modified in Usf2−/−mice compared to wild-type mice (FIG. 3B).

The level of ceruloplasmin, heme oxygenase 1 and transferrin receptor mRNAs was also monitored in Usf2−/−mice, since the abundance of these mRNAs has been reported to be modified in disorders that disturb iron balance (for review see ANDREWS et al., Nutr. Rev., 57, 114-123, 1999). Again it was found that the level of these mRNAs was comparable in Usf2−/− and control mice.

Finally, the expression of the DMT1 gene (also referred to as Nramp2), the major transmembrane iron uptake protein that actively transports reduced dietary iron into intestinal enterocytes was analyzed. Duodenal expression of DMT1 was analyzed by relative quantification using RT-PCR (7 Usf2−/− versus 6 control mice). No statistically significant differences were found between the two groups of mice (not shown).

Analysis of Subtraction cDNA Libraries: Identification of Hepcidin as a Putative Candidate for Hemochromatosis To identify genes whose level of expression is modified in Usf2−/−mice, a subtracted cDNA library between liver from Usf2−/−(driver) and wild-type (tester) mice (DIATCHENKO, Proc. Natl. Acad. Sci. USA, 93, 6025-6030, 1996) was performed. Among 400 clones analyzed, several clones were down-regulated in the liver from Usf2−/−mice as analyzed by reverse Northern blot (not shown). One of these clones contained a full-length cDNA encoding the recently characterized peptide hepcidin (KRAUSE et al., FEBS Lett., 480, 147-150, 2000; PARK et al., J. Biol. Chem., 276, 7806-7810, 2001; PIGEON et al., J. Biol. Chem., 276, 7811-7819, 2001).

Murine Organization of Usf2 and Hepcidin Genes on Chromosome 7

The murine genome contains two closely related hepcidin genes that colocalize on the same mouse genomic clone (Genbank clone, accession number AC020841). These genes were designated HEPC1 and HEPC2 by PIGEON et al. (J. Biol. Chem., 276, 7811-7819, 2001). Interestingly, the genomic CT7-8N15 clone also revealed that HEPC1 is situated in close proximity to the Usf2 gene on murine chromosome 7. PIGEON et al reported that HEPC1 was located directly downstream of the Usf2 gene (PIGEON et al., J. Biol. Chem., 276, 7811-7819, 2001). By analysing another genomic clone, RP23-22G9 (Genbank, accession number AC087143), it was found that part of the Usf2 gene (encompassing exons 8, 9 and 10) was also duplicated and that, in fact, HEPC1 lies downstream of the truncated Usf2 gene.

Figure 4:
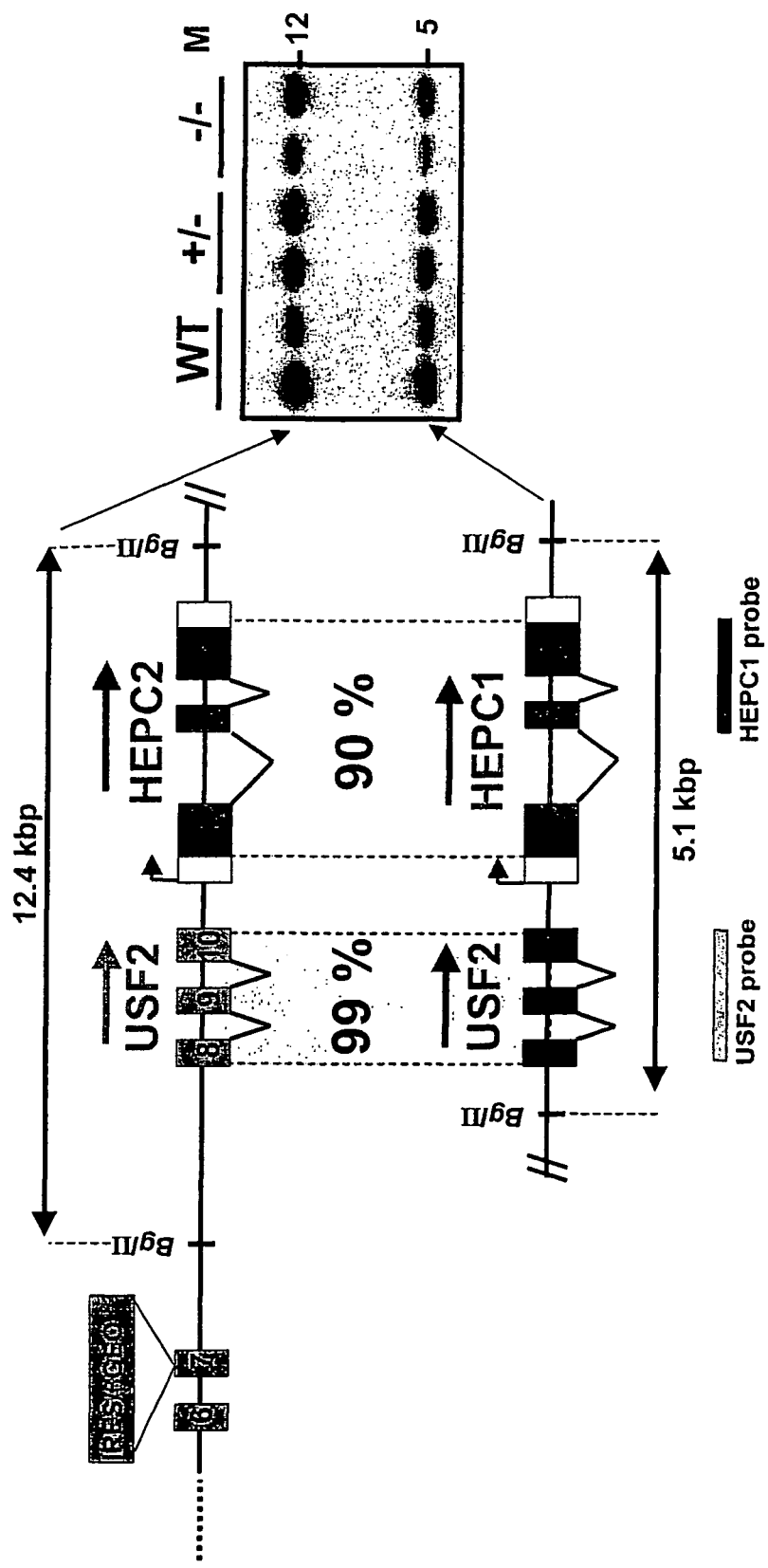
FIG. 4 shows the genomic organization of Usf2 and hepcidin genes.

The genomic organization of Usf2 and hepcidin genes is shown in FIG. 4.

Legend of FIG. 4:

Schematic representation (not to scale) of the locus region encompassing the Usf2 and hepcidin genes. The targeted allele is represented with the betageo cassette insertion in exon 7 (VALLET et al., J. Biol. Chem., 272, 21944-21949, 1997). Data are resulting from genomic RP23-22G9 clone (Genbank). So far, no data are available concerning the orientation and the distance between the two hepcidin genes. The Southern blot in the right of the Figure is from tail DNA of wild-type, heterozygote and homozygote mice digested by BglII and hybridized with the HEPC1 probe. Two bands of the expected size, 12.4 kbp and 5.1 kbp, were detected, whatever the genotype. The same bands were revealed using the USF2 probe.

The HEPC2 gene is located downstream of the functional complete Usf2 gene and the HEPC1 gene is located downstream of the partial Usf2 gene. At present, no information is available concerning the relative orientation 5'-3' of the HEPC1 and HEPC2 genes and the distance between them.

Because of the proximity of the Usf2 gene and hepcidin locus, it was determined whether the recombination event in intron 7 of the targeted Usf2 allele might have eliminated or truncated the HEPC1 and HEPC2 genes. To check this hypothesis, Southern blot was performed on genomic tail DNA from wild-type, Usf2+/− or Usf2−/−mice with an HEPC1 probe (FIG. 4). Genomic DNA was digested by BglII. Based on the analysis of the AC087143 locus, this digestion was predicted to generate two fragments of 5.1 and 12.4 kbp, containing the HEPC1 and HEPC2 genes, respectively. Due to the close similarity (more than 95%) between the hybridizing region of HEPC1 and HEPC2, both bands were expected to be revealed by the HEPC1 probe. This is what was found, as shown on the Southern blot in FIG. 4. The same pattern was observed with DNA from Usf2−/−mice indicating that the hepcidin genes are present in Usf2−/−mice and that they have not undergone major rearrangement. Finally, the two bands also hybridized with an USF2 probe extending from exon 8 to exon 10, demonstrating that exons 8 to 10 of USF2 are indeed duplicated.

The Hepcidin Genes are Totally Silent in the Liver of Usf2−/− Mice

The level of expression of the hepcidin genes was measured by Northern blot analysis. In fact, hepcidin mRNA was totally undetectable in the liver of Usf2−/−mice (FIG. 5A). It is worth noting that the liver of Usf2+/− mice contained a reduced amount of hepcidin mRNA compared with wild-type mice. To further assess the specific level of HEPC1 and HEPC2 messengers, specific primers for the HEPC1 and HEPC2 transcripts were designed. By RT-PCR it was demonstrated that both genes were actively transcribed in the liver of wild-type mice (FIG. 5B-C) while both HEPC1 and HEPC2 transcripts were totally absent from the liver of Usf2−/−mice (FIG. 5B-C)

Figure 5:
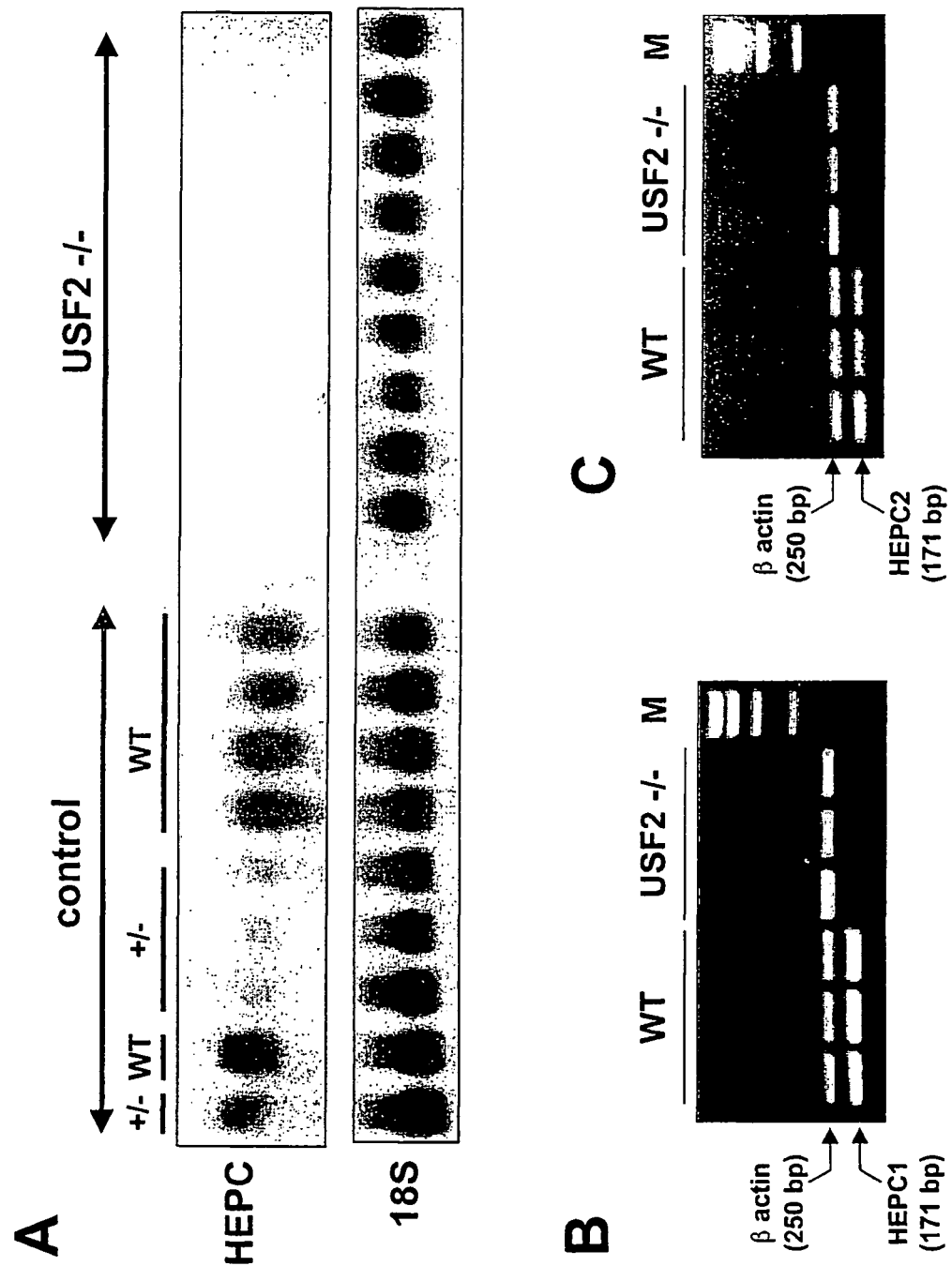
FIG. 5 shows the level of expression of the hepcidin genes.

Legend of FIG. 5:

(A) Twenty micrograms of total liver RNAs from wild-type, Usf2+/− and Usf2−/−animals (between 3- and 11-month-old) were electrophoresed and blotted. The blot was hybridized with a 32P-labeled HEPC probe (prepared as described in "Materials and Methods") which most likely recognized both HEPC1 and HEPC2 transcripts. (B) Specific HEPC1 and HEPC2 levels were measured by RT-PCR as described in materiel and Methods. Following PCR, the amplified products (171 bp for HEPC1 or HEPC2 and 250 bp for β-actin) were separated by electrophoresis on 1.5% agarose gel. Neither HEPC1 nor HEPC2 specific primers were able to reamplify HEPC2 and HEPC1 PCR products, respectively, demonstrating the high specificity of each pair of primers (not shown).

Figure 6:
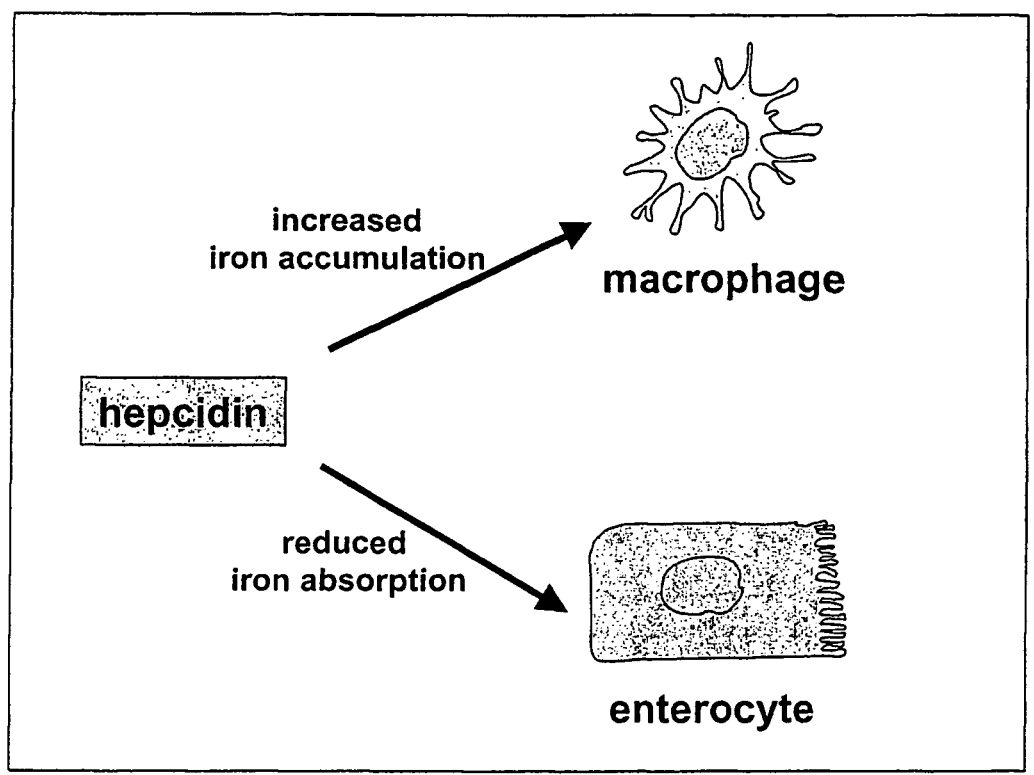
FIG. 6 shows a proposed model of relating hepcidin to intestinal iron absorption and macrophage iron stores.

The similarity of the alterations in iron metabolism between HFE knockout mice and the Usf2−/−hepcidin deficient mice suggests that hepcidin may function in the same regulatory pathway as HFE. It has been shown that HFE physically interacts with the transferrin receptor in crypt cells of the duodenal mucosa (WAHEED et al., Proc. Natl. Acad. Sci. USA, 96, 1579-1584, 1999). Without being bound by theory, it may be postulated that this interaction modulates the iron status of these cells which, in turn, controls the expression of the apical and basolateral transporters in mature cells at the tips of the villi. Hepcidin may be required for HFE activity perhaps through direct interaction with the HFE/beta2 microglobulin/transferrin receptor complex. Similarly, hepcidin may be required for the regulation of iron storage in macrophages. The presence of a mutated HFE protein or a complete defect in hepcidin expression may be responsible for increased intestinal iron absorption and reduced macrophage iron stores, according to the model shown in FIG. 6.

In this model, hepcidin prevents iron overload by reducing iron transport in the enterocyte and by programming macrophages to retain iron. In Usf2−/−mice, the hepcidin defect would be responsible for increased intestinal iron transport and reduced macrophage iron stores.

Under both conditions, plasma iron overcomes transferrin binding capacity and non-transferrin bound iron accumulates in various tissues including heart and pancreas.

According to the proposed role of hepcidin in iron homeostasis, hepcidin production may depend on the uptake of transferrin-bound iron mediated by TFR2 in hepatocytes. This might explain why the TFR2 defect is responsible for a form of human genetic hemochromatosis if this defects leads to a decrease in hepcidin secretion that, in turn, results in increased iron absorption. This hypothesis will be testable by measuring plasma hepcidin in patients with TFR2 deficiency or in TFR2 knockout mice.

EXAMPLE 2

Characteristics of Transgenic Mice Overexpressing Hepcidin

Methods
Generation of Transgenic Mice

Full length cDNA of the murine hepc1 cDNA was amplified using primers

```
                                         (SEQ ID NO: 34)
5'-GGGGGATATCAGGCCTCTGCACAGCAGAACAGAAGG-3'
and (SEQ ID NO: 35)
5'-GGGGGATATCAGGCCTCTATGTTTTGCAACAGATACC-3'.
```

Both primers contain a StuI site (underlined).

The hepc1 PCR fragment was introduced between the mouse transthyretin (TTR) promoter (consisting of the first exon, first intron and most of the second exon) and the SV40 small-T poly(A) signal cassette. The construct carries 3 kb of mouse TTR DNA sequences 5' to the cap site (YAN et al., EMBO J., 9, 869-879, 1990). The 4.7 kbp TTR-hepc1 transgene was separated from plasmide sequence by digestion with HindIII and used for pronuclear microinjection.

Genotyping by PCR and Southern Blotting

Southern blotting was done according to standard methods (SAMBROOK et al., Molecular Cloning, A Laboratory Manual, 2nd Ed., Cold Spring Harbor Laboratory Press: 1989). Genomic DNA was prepared from tail as follow: a 5-mm piece of tail was cut from each mouse and placed into 500 µl of digestion mix (50 mM Tris, pH 8/100 mM EDTA/100 mM NaCl/1% SDS). Proteinase K (200 µg) was added and digestion was performed at 55° C. overnight. The samples were extracted directly by adding 500 µl of phenol/chloroform/isoamyloalcohol (1/24/25). After vortexing and centrifugation, clear aqueous phase was precipitated with one volume of isopropanol. For southern blotting, DNA was digested by BamHI, which cut twice the transgene. After electrophoresis, DNA was transferred to a nylon membrane (Hybond-N+, Amersham). Probe corresponds to the 1.7 kbp BglII-HindIII fragment from the previously described TTR plasmid (YAN et al., EMBO J., 9, 869-878, 1990). The probe were labelled with dCTP $^{32}$P with random priming, using a commercially available kit (DNA Labeling System, Gibco). The 5.3 kbp labelled fragment correspond to endogenous TTR gene and the 4.7 kbp labelled fragment corresponds to the transgene.

For PCR reaction, genomic DNA (0.5-1 µg) was utilized in 25 µl reactions which included two primers: TTR-hepc1 transgene was amplified using primers:

```
5'-CTTTTTGCACCATGCACCTTTC-3'    (SEQ ID NO: 36;
                                 annealing in
                                 intron 1 of TTR)
and 5'-AACAGATACCACACTGGGAA-3'      (SEQ ID NO: 37;
                                 annealing in
                                 hepc1 cDNA).
```

PCR reaction was performed as following: 25 cycles (each cycle consist of 40 seconds at 94° C., 40 seconds at 50° C. and 40 seconds at 72° C.) with an initial denaturation step at 94° C. for 4 minutes and a final elongation step at 72° C. for 5 minutes in 20 mM Tris-HCl (pH 8.4), 50 mM KCl, 0.05% W-I, 2 mM MgCl$_2$, 0.2 mM each dNTP, 0.2 µM each primer, 2 units of Taq polymerase (Gibco). The 612 bp specific product was amplified with a non specific fragment of the same size. The presence of the transgene is revealed after digestion of the PCR product with 10 units of StuI during 2 hours that produces 268 bp and 344 bp. Reaction was analyzed on 1.5-2% agarose gel containing ethidium bromide. The amplification of the non specific fragment ensure that the absence of transgene is not due to the lack or degradation of genomic DNA. This PCR method for mouse genotyping was found to give the same results as the Southern blot method.

Results
Characteristics of TTR-hepc1 Transgenic Mice

A total of nine independent transgenic founder mice were produced by classical microinjection method of a linearized construct.

The construct is schematically represented in FIG. 7A.

FIG. 7B shows a Southern blot with the different founders.

Three transgenic mice founders (TH27, TH37 and TH52) were indistinguishable from their wild-type mice (Wt) littermate. Three transgenic mice founders were born with a pallor skin and died within a few hours after birth (bb2, 3 and 5). Finally, the phenotype of the three last transgenic mice founders (TH5, 35, and 44) was unambigous: they had a hairloss on whole body and their skin was crumpled. Blood smears were performed on these animals and evidences of strong poikylocytosis and hypochromia were found in the three mice with the crumpled skin.

The above examples highlight the role of hepcidin as a key regulator of iron homeostasis. Hepcidin is proposed as a novel candidate gene that, when mutated, could be involved in abnormal regulation of iron metabolism and development of HH. Finally, the new murine model of iron overload disease disclosed above appears to be a suitable animal model for testing new therapeutic approaches for prevention and correction of the iron storage in HH as well as for the understanding of iron homeostasis.

The invention claimed is:

1. A pharmaceutical composition for parenteral administration comprising (a) an antibody that binds a human hepcidin peptide comprising the amino acid sequence set forth in SEQ ID NO: 3 and that is capable of inhibiting the activity of hepcidin and (b) a suitable carrier or excipient,
   wherein the composition is for administration by intramuscular, subcutaneous, intravenous or intraperitoneal injection.

* * * * *

SEQUENCE LISTING

<160> NUMBER OF SEQ ID NOS: 37

<210> SEQ ID NO 1
<211> LENGTH: 20
<212> TYPE: PRT
<213> ORGANISM: Homo sapiens

<400> SEQUENCE: 1

Ile Cys Ile Phe Cys Cys Gly Cys Cys His Arg Ser Lys Cys Gly Met
1               5                   10                  15

Cys Cys Lys Thr
            20

<210> SEQ ID NO 2
<211> LENGTH: 22
<212> TYPE: PRT
<213> ORGANISM: Homo sapiens

<400> SEQUENCE: 2

Phe Pro Ile Cys Ile Phe Cys Cys Gly Cys Cys His Arg Ser Lys Cys
1               5                   10                  15

Gly Met Cys Cys Lys Thr
            20

<210> SEQ ID NO 3
<211> LENGTH: 25
<212> TYPE: PRT
<213> ORGANISM: Homo sapiens

<400> SEQUENCE: 3

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 4
<211> LENGTH: 20
<212> TYPE: DNA
<213> ORGANISM: Mus sp.

<400> SEQUENCE: 4
gcgaagccct gggttcaatc                                           20

<210> SEQ ID NO 5
<211> LENGTH: 21
<212> TYPE: DNA
<213> ORGANISM: Mus sp.

<400> SEQUENCE: 5
ggggtccacc acttcaagag g                                         21

<210> SEQ ID NO 6
<211> LENGTH: 20
<212> TYPE: DNA
<213> ORGANISM: Mus sp.

<400> SEQUENCE: 6
gcgaagccct gggttcaatc                                          20

<210> SEQ ID NO 7
<211> LENGTH: 22
<212> TYPE: DNA
<213> ORGANISM: Mus sp.

<400> SEQUENCE: 7
gaattctcta gagcggccgg ac                                       22

<210> SEQ ID NO 8
<211> LENGTH: 26
<212> TYPE: DNA
<213> ORGANISM: Mus sp.

<400> SEQUENCE: 8
caggaaacag ctatgaccat gattac                                   26

<210> SEQ ID NO 9
<211> LENGTH: 23
<212> TYPE: DNA
<213> ORGANISM: Mus sp.

<400> SEQUENCE: 9
taatacgact cactataggg cga                                      23

<210> SEQ ID NO 10
<211> LENGTH: 20
<212> TYPE: DNA
<213> ORGANISM: Mus sp.

<400> SEQUENCE: 10
cctatctcca tcaacagatg                                          20

<210> SEQ ID NO 11
<211> LENGTH: 20
<212> TYPE: DNA
<213> ORGANISM: Mus sp.

<400> SEQUENCE: 11
aacagatacc acactgggaa                                          20

<210> SEQ ID NO 12
<211> LENGTH: 20
<212> TYPE: DNA
<213> ORGANISM: Mus sp.

<400> SEQUENCE: 12
cctatctcca gcaacagatg                                          20

<210> SEQ ID NO 13
<211> LENGTH: 20
<212> TYPE: DNA
<213> ORGANISM: Mus sp.

<400> SEQUENCE: 13
aacagatacc acaggagggt                                          20

<210> SEQ ID NO 14
<211> LENGTH: 20
<212> TYPE: DNA
<213> ORGANISM: Mus sp.

-continued

```
<400> SEQUENCE: 14
agccatgtac gtagccatcc                                              20

<210> SEQ ID NO 15
<211> LENGTH: 20
<212> TYPE: DNA
<213> ORGANISM: Mus sp.

<400> SEQUENCE: 15
tttgatgtca cgcacgattt                                              20

<210> SEQ ID NO 16
<211> LENGTH: 18
<212> TYPE: DNA
<213> ORGANISM: Mus sp.

<400> SEQUENCE: 16
tcctggactg tggacgct                                                18

<210> SEQ ID NO 17
<211> LENGTH: 24
<212> TYPE: DNA
<213> ORGANISM: Mus sp.

<400> SEQUENCE: 17
ggtgttcaga agatagagtt cagg                                         24

<210> SEQ ID NO 18
<211> LENGTH: 21
<212> TYPE: DNA
<213> ORGANISM: Mus sp.

<400> SEQUENCE: 18
tgtttgattg cattgggtct g                                            21

<210> SEQ ID NO 19
<211> LENGTH: 20
<212> TYPE: DNA
<213> ORGANISM: Mus sp.

<400> SEQUENCE: 19
cgctcagcag gactttcgag                                              20

<210> SEQ ID NO 20
<211> LENGTH: 19
<212> TYPE: DNA
<213> ORGANISM: Mus sp.

<400> SEQUENCE: 20
caggaccaag acccctgga                                               19

<210> SEQ ID NO 21
<211> LENGTH: 18
<212> TYPE: DNA
<213> ORGANISM: Mus sp.

<400> SEQUENCE: 21
atcttcatcc cagagcga                                                18

<210> SEQ ID NO 22
<211> LENGTH: 20
<212> TYPE: DNA
<213> ORGANISM: Mus sp.
```

<400> SEQUENCE: 22
atgagcctat cagctgggct                                               20

<210> SEQ ID NO 23
<211> LENGTH: 20
<212> TYPE: DNA
<213> ORGANISM: Mus sp.

<400> SEQUENCE: 23
tcactcacag tctgttaaga                                               20

<210> SEQ ID NO 24
<211> LENGTH: 20
<212> TYPE: DNA
<213> ORGANISM: Mus sp.

<400> SEQUENCE: 24
gaaatccctg tctgttatac                                               20

<210> SEQ ID NO 25
<211> LENGTH: 20
<212> TYPE: DNA
<213> ORGANISM: Mus sp.

<400> SEQUENCE: 25
ggcaaagctg aaagcatttc                                               20

<210> SEQ ID NO 26
<211> LENGTH: 19
<212> TYPE: DNA
<213> ORGANISM: Mus sp.

<400> SEQUENCE: 26
tacagctcgg agcggaacg                                                19

<210> SEQ ID NO 27
<211> LENGTH: 20
<212> TYPE: DNA
<213> ORGANISM: Mus sp.

<400> SEQUENCE: 27
ttacaatctc aggcacctcc                                               20

<210> SEQ ID NO 28
<211> LENGTH: 20
<212> TYPE: DNA
<213> ORGANISM: Mus sp.

<400> SEQUENCE: 28
acttatttca gttgacacgg                                               20

<210> SEQ ID NO 29
<211> LENGTH: 20
<212> TYPE: DNA
<213> ORGANISM: Mus sp.

<400> SEQUENCE: 29
gcagcacata cacatactgt                                               20

<210> SEQ ID NO 30
<211> LENGTH: 19
<212> TYPE: DNA

```
<213> ORGANISM: Mus sp.

<400> SEQUENCE: 30
atggagcgtc cacagcccg                                                    19

<210> SEQ ID NO 31
<211> LENGTH: 20
<212> TYPE: DNA
<213> ORGANISM: Mus sp.

<400> SEQUENCE: 31
ccttcggtgc agctcctcag                                                   20

<210> SEQ ID NO 32
<211> LENGTH: 21
<212> TYPE: DNA
<213> ORGANISM: Mus sp.

<400> SEQUENCE: 32
gagcagcacc acctatctcc a                                                 21

<210> SEQ ID NO 33
<211> LENGTH: 20
<212> TYPE: DNA
<213> ORGANISM: Mus sp.

<400> SEQUENCE: 33
aacagatacc acaggagggt                                                   20

<210> SEQ ID NO 34
<211> LENGTH: 36
<212> TYPE: DNA
<213> ORGANISM: Mus sp.

<400> SEQUENCE: 34
gggggatatc aggcctctgc acagcagaac agaagg                                 36

<210> SEQ ID NO 35
<211> LENGTH: 37
<212> TYPE: DNA
<213> ORGANISM: Mus sp.

<400> SEQUENCE: 35
gggggatatc aggcctctat gttttgcaac agatacc                                37

<210> SEQ ID NO 36
<211> LENGTH: 22
<212> TYPE: DNA
<213> ORGANISM: Mus sp.

<400> SEQUENCE: 36 cttttttgcac catgcaccttt tc                                              22

<210> SEQ ID NO 37
<211> LENGTH: 20
<212> TYPE: DNA
<213> ORGANISM: Mus sp.

<400> SEQUENCE: 37
aacagatacc acactgggaa                                                   20
```